United States Patent
Hussein

(10) Patent No.: US 11,806,381 B2
(45) Date of Patent: Nov. 7, 2023

(54) EFFICACY OF GARLIC THERAPY IN CONTROLLING INFLAMMATORY CYTOKINES AND CARTILAGE DEGRADATION IN KNEE OSTEOARTHRITIS AND IMPROVING QUALITY OF LIFE

(71) Applicant: Naglaa Hussein, New Rochelle, NY (US)

(72) Inventor: Naglaa Hussein, New Rochelle, NY (US)

( * ) Notice: Subject to any disclaimer, the term of this patent is extended or adjusted under 35 U.S.C. 154(b) by 164 days.

(21) Appl. No.: 17/172,650

(22) Filed: Feb. 10, 2021

(65) Prior Publication Data
US 2022/0249590 A1    Aug. 11, 2022

(51) Int. Cl.
*A61K 36/8962* (2006.01)
*A23L 33/105* (2016.01)
*A61K 9/00* (2006.01)
*A61P 19/02* (2006.01)
*A23L 33/00* (2016.01)

(52) U.S. Cl.
CPC ........ *A61K 36/8962* (2013.01); *A23L 33/105* (2016.08); *A23L 33/30* (2016.08); *A61K 9/0053* (2013.01); *A61P 19/02* (2018.01)

(58) Field of Classification Search
None
See application file for complete search history.

(56) References Cited

PUBLICATIONS

Boffa et al. (2021) Cartilage vol. 13 (Suppl. 1): 82S-103S. (Year: 2021).*
Dehghani et al. (2018) Phytomedicine 48: 70-75. (Year: 2018).*
Hosseinzadeh-Attar et al. (2020) J. Herbal Med. 24: 100392 (4 pages). (Year: 2020).*
Sauerschnig et al. (2014) Eur. J. Med. Res. 19: 65 (6 pages). (Year: 2014).*
Tavakoli-Far et al. (2021) BRIAC vol. 11, Issue 4: 12104-12119. (Year: 2021).*
Yang et al. (2021) Cytokine 143: 155546. (10 pages) (Year: 2021).*

* cited by examiner

*Primary Examiner* — Russell G Fiebig
(74) *Attorney, Agent, or Firm* — Derek Fahey, Esq.; The Plus IP Firm, PLLC

(57) ABSTRACT

Methods for treating knee osteoarthritis in a patient are disclosed. In one embodiment, a method for treating a knee osteoarthritis patient using an oral dried garlic supplement, wherein the treating comprises administering 900 mg of the oral dried garlic supplement on a daily basis. In one embodiment, 1800 mg of the oral dried garlic supplement is used.

5 Claims, No Drawings

EFFICACY OF GARLIC THERAPY IN CONTROLLING INFLAMMATORY CYTOKINES AND CARTILAGE DEGRADATION IN KNEE OSTEOARTHRITIS AND IMPROVING QUALITY OF LIFE

CROSS-REFERENCE TO RELATED APPLICATIONS

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The present invention relates to intelligent systems, and more specifically, to the field of systems for automated assistance with virtual content.

BACKGROUND

Primary knee osteoarthritis ("KOA") is a disorder affecting roughly 12.4 million people in the United States. Knee symptoms can vary depending on the cause of the problem. The most common symptom of KOA is pain around the knee joint. This pain may either be dull, sharp, constant, or pulsating. Other symptoms include swelling, locking, and giving way of the knee. These disabilities, mainly related to pain, ultimately manifest with difficulty in walking, climbing stairs, performing household chores, and sitting upright and have a negative psychological impact, all of which can lead to a decreased quality of life. Furthermore, those suffering from KOA can also experience a decreased range of motion in their knee joint.

Traditionally, KOA was thought to be a consequence of aging, thus leading to its categorization as a degenerative knee disease. However, recently it has been determined that the pathogenesis of KOA is multifactorial. The suggested etiological factors include genetic, age, obesity, and occupation, joint malalignment. Although knee osteoarthritis is closely correlated with aging, it is important to note that knee osteoarthritis is not simply a consequence of aging, but rather its own disease. This is supported by the differences seen in cartilage with both osteoarthritis and aging. Furthermore, the enzymes responsible for cartilage degradation are expressed in higher amounts in knee osteoarthritis, whereas they are at normal levels in the normal aging cartilage.

It is often necessary for those suffering from KOA to avoid high-impact activities and switching to lower-impact activities to diminish stress on the knee and improve the symptoms. Additionally, weight loss may be beneficial for reducing pain in overweight patients. Multiple surgical options are available for treating patients with KOA and include techniques such as arthroscopy, cartilage repair, osteotomies, and knee replacement. However, it is not always possible for those with KOA to avoid high-impact activities, moreover, surgical options may be inadvisable for many patients; thus, highlighting the need for alternative, chemotherapeutic, approaches to treating KOA.

Current chemotherapeutic approaches to treating KOA involve the use of NSAIDs such as ibuprofen, naproxen, diclofenac, and/or aspirin. Glucosamine and chondroitin sulfate are available as dietary supplements. They are structural components of articular cartilage, and the thought is that a supplement will aid in the health of articular cartilage. Intra-articular corticosteroid injections may be useful for symptomatic knee osteoarthritis, especially where there is a considerable inflammatory component. The delivery of the corticosteroid directly into the knee may reduce local inflammation associated with osteoarthritis and minimize the systemic effects of the steroid. Intra-articular hyaluronic acid injections ("HA") injections are another option for treating KOA. HA is a glycosaminoglycan that is found throughout the human body and is an important component of synovial fluid and articular cartilage.

Existing chemotherapeutic approaches to treating KOA have a number of problems. One such problem emerges from the low therapeutic index of current chemotherapeutic options. Additionally, current chemotherapeutic options are incapable of inhibiting multiple targets responsible for the pathogenesis of KOA. As a result of chemotherapeutic options of KOA are restrictive in that they may only be administered to those who in good health.

As a result, there exists a critical need for improvements over the prior art and more particularly for chemotherapeutic treatments for KOA capable of inhibiting MMPs and cytokine production whilst maintaining a high therapeutic index.

SUMMARY

A method for treating knee osteoarthritis in a patient using a dried garlic supplement is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

Methods for treating a knee osteoarthritis are disclosed. In one embodiment, a method for treating a knee osteoarthritis patient using an oral dried garlic supplement, wherein the treating comprises administering 900 mg of the oral dried garlic supplement on a daily basis. In one embodiment, method for treating a knee osteoarthritis patient using an oral dried garlic supplement, wherein the treating comprises administering 1800 mg of the oral dried garlic supplement on a daily basis. In one embodiment, method for treating a knee osteoarthritis patient using an oral dried garlic supplement, wherein the treating comprises (a) performing an initial synovial fluid analysis and an initial serum analysis on the knee osteoarthritis patient, (b) administering 900 to 1800 mg of the oral dried garlic supplement on a daily basis and for eight weeks or more, and (c) after the eight weeks or more, performing a final synovial fluid analysis and a final serum analysis.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

Not applicable; no drawings are submitted herewith.

DETAILED DESCRIPTION

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing a method for treating knee osteoarthritis in a patient using a dried garlic supplement that is more effective, cheaper, and more natural than existing methods. While the disclosed methods are described as being applicable to knee osteoarthritis, it is believed that the methods may be applicable to other forms of osteoarthritis.

In one embodiment, a method for treating a knee osteoarthritis patient using an oral dried garlic supplement, wherein the treating comprises administering 900 mg of the oral dried garlic supplement on a daily basis. In one embodiment, a method comprises reducing inflammation as shown by reduction of effusion in the knee osteoarthritis patient by above 50%, and wherein the method comprises reducing a pain score by above 50%, wherein the pain score is measured using a visual analogue scale ("VAS"). In one embodiment, a method additionally comprises a routine exercise regimen for the knee osteoarthritis patient, and wherein the method comprises improving muscle strength in the knee osteoarthritis patient, wherein the improving muscle strength comprises increasing a quadricep 1RM by above 50%. In one embodiment, a method additionally comprises improving a quality-of-life score by above 50%, wherein the quality-of-life score is measured using a Stanford Health Assessment Questionnaire ("HAQ"). In one embodiment, relative to a control patient treated by a glucosamine sulfate treatment, the method additionally comprises realizing a significant improvement of inflammatory cytokines, cartilage degrading enzymes, inflammation as shown by reduction of effusion, pain score, muscle strength, and quality-of-life score.

In one embodiment, an exercise program includes performed the following exercise program at our department for 3 sessions per week on alternate days, for 8 weeks: (1) Flexibility exercise: patients performed static stretching of both hamstrings and quadriceps muscles before the dynamic resistance exercise, (2) Dynamic resistance exercise for quadriceps: using Cybex weight machine was conducted after electro-analgesia and flexibility exercises. Exercise was carried out at intensity of 40% of 1 RM for 8 repetitions. The 1RM measurement was repeated every 2 weeks so that the intensity of resistance exercise was kept at constant level throughout the eight weeks. In addition, all patients were instructed to perform the same flexibility exercise at home on the remaining days of the week.

In one embodiment, a method for treating a knee osteoarthritis patient using an oral dried garlic supplement, wherein the treating comprises administering 1800 mg (e.g., 1400-2200 mg, 1600-2000 mg) of the oral dried garlic supplement on a daily basis. It is believed that although a daily dose of the oral dried garlic supplement of 900 mg is effective in treating knee osteoarthritis, increasing the dose by around two times (e.g., 1800 mg) has unexpectedly been discovered as being more effective in all measured properties (discussed below). In one embodiment, prior to administering the 1800 mg of the oral dried garlic supplement on a daily basis the method comprises measuring an initial level of inflammatory cytokines and inflammatory markers comprising IL1$\beta$, IL6, TNF-$\alpha$ and nitric oxide, and wherein after 8 weeks of treating the knee osteoarthritis patient, a final level of inflammatory cytokines and inflammatory markers is significantly reduced by above 50% relative to the initial level of inflammatory cytokines and inflammatory markers. In one embodiment, prior to administering the 1800 mg of the oral dried garlic supplement on a daily basis the method comprises measuring an initial level of cartilage degrading enzymes comprising MMP13, wherein after 8 weeks of treating the knee osteoarthritis patient, a final level of cartilage degrading enzymes is reduced by above 50%, relative to the initial level of cartilage degrading enzymes. In one embodiment, prior to administering the 1800 mg of the oral dried garlic supplement on a daily basis the method comprises measuring an initial level of glutathione peroxidase, and wherein after 8 weeks of treating the knee osteoarthritis patient, a post-treatment level of glutathione peroxidase is reduced by above 50%, relative to the initial level of glutathione peroxidase. In one embodiment, the method additionally comprises reducing inflammation, as shown by reduction of effusion, in the knee osteoarthritis patient by above 50%, and wherein the method comprises reducing a pain score by above 50%, wherein the pain score is measured using a visual analogue scale ("VAS"). In one embodiment, the method additionally comprises improving quality-of-life score by above 50%, wherein the quality-of-life score is measured using at least one of Stanford Health Assessment Questionnaire ("HAQ") and a Lequesne index functional score.

In one embodiment, a method for treating a knee osteoarthritis patient using an oral dried garlic supplement, wherein the treating comprises (a) performing an initial synovial fluid analysis and an initial serum analysis on the knee osteoarthritis patient, (b) administering 900 to 1800 mg of the oral dried garlic supplement on a daily basis and for eight weeks or more, and (c) after the eight weeks or more, performing a final synovial fluid analysis and a final serum analysis. In one embodiment, the amount of the oral dried garlic supplement is 1800 mg (e.g., 1400-2200 mg, 1600-2000 mg). The amount of oral dried garlic supplement far exceeds that would be possible by eating garlic in foods.

In one embodiment, the initial and final synovial fluid analyses comprise measuring a level of inflammatory cytokines and inflammatory markers comprising IL1$\beta$, IL6, TNF-$\alpha$, and nitric oxide ("NO"), (i) wherein the administering comprises administering 900 mg of the oral dried garlic supplement, wherein a final level of inflammatory markers and inflammatory cytokines is reduced by above 50%, (ii) wherein the administering comprises administering 1800 mg of the oral garlic supplement, wherein the final level of inflammatory markers and inflammatory cytokines is reduced by above 80%, and wherein the final level of inflammatory markers and inflammatory cytokines in administering the 1800 mg of the oral dried garlic supplement is statistically significantly lower than the final level of inflammatory markers and inflammatory cytokines in administering the 900 mg of the oral dried garlic supplement.

In one embodiment, the initial and final serum analyses comprise measuring a level of cartilage degrading enzymes comprising MMP13, wherein (i) the administering comprises administering 900 mg of the oral dried garlic supplement, wherein a final level of cartilage degrading enzymes is reduced by above 50%, and (ii) the administering comprises administering 1800 mg of the oral directed garlic supplement, wherein the final level of cartilage degrading enzymes is reduced by above 80%, and (iii) the final level of cartilage degrading enzymes in administering the 1800 mg of the oral dried garlic supplement is statistically significantly lower than the final level of cartilage degrading enzymes in administering the 900 mg of the oral dried garlic supplement.

In one embodiment, wherein the method comprises measuring an initial Lequesne index functional score, and wherein after the eight weeks or more, measuring a final Lequesne index functional score, wherein: (i) the administering comprises administering 900 mg of the oral dried garlic supplement, wherein the final Lequesne index functional score is improved by above 50%, (ii) the administering comprises administering 1800 mg of the oral directed garlic supplement, wherein the final Lequesne index functional score is improved by above 80%, and (iii) the final Lequesne index functional score in administering the 1800 mg of the oral dried garlic supplement is statistically significantly improved relative to the final Lequesne index functional score in administering the 900 mg of the oral dried garlic supplement.

In one embodiment, the initial and final synovial fluid analyses comprise measuring a level of glutathione peroxidase, wherein: (i) the administering comprises administering 900 mg of the oral dried garlic supplement, wherein a final level of glutathione peroxidase is improved by above 50%, (ii) the administering comprises administering 1800 mg of the oral directed garlic supplement, wherein the final level of glutathione peroxidase is improved by above 80%, and (iii) the final level of glutathione peroxidase in administering the 1800 mg of the oral dried garlic supplement is statistically significantly improved relative to the final level of glutathione peroxidase in administering the 900 mg of the oral dried garlic supplement.

In one embodiment, the initial and post-treatment synovial fluid analyses comprise measuring a level of selenium, wherein: (i) the administering comprises administering 900 mg of the oral dried garlic supplement, wherein a final level of selenium is increased by above 50%, (ii) the administering comprises administering 1800 mg of the oral directed garlic supplement, wherein the final level of selenium is increased by above 80%, and (iii) the final level of selenium in administering the 1800 mg of the oral dried garlic supplement is statistically significantly increased relative to the final level of selenium in administering the 900 mg of the oral dried garlic supplement.

i. Summary of the Nature of Knee Osteoarthritis

The etiology of primary knee osteoarthritis ("KOA") is multifactorial. There is no single factor involved.[1] The suggested etiological factors include genetic, age, obesity, and occupation, joint malalignment It is now established that the pathophysiology of KOA involves inflammatory process.

The pathophysiology of osteoarthritis ("OA") is a complex network. It is believed that cytokines IL1β and TNF-α initiate a vicious cycle of catabolic and degradative events in cartilage mediated by metalloproteinases which degrade the extracellular matrix. In addition to excessive production of nitric oxide and prostaglandin $E_2$ that are augmented by cytokines. Oxidative stress and free radical activity have strong contribution to the severity of clinical signs of osteoarthritis[1].

In knee osteoarthritis, high activity of glutathione peroxidase is part of the increase of antioxidant enzymes as a compensatory regulation in response to increased oxidative stress IL1β markedly enhance superoxide dismutase and glutathione peroxidase gene expression[1].

ii. Biochemical Changes of Osteoarthritis

The progression of early OA to later OA: One first step of cartilage degradation is a decrease in the density of proteoglycans. This is partly reversible, however the decreased proteoglycan density opens up the cartilage porosity to make it more permeable to collagenase and other proteases. It exposes collagen. This instates a vicious circle of positive feedback loop for further enzymes to promote cartilage degradation. Epitope on collagen became accessible to DDR2 receptor on cell surface which then increases matrix metalloproteinase MMP13 production.[1] Through activation of RAS/RAF. MEK/ERK and p38 signal cascade.[1]

There is increased synthesis and activation of matrix degrading enzymes and overall decrease in the concentration of enzyme inhibitors such as tissue inhibitor of metalloproteinase TIMP.

Cartilage remodeling also involves a degree of proteolysis. This occurs via the induction of array of proteinase proteases. In particular MMPs, cytokines IL1β and TNF-α stimulate synthesis and section of many proteases and MMP.[1]

Interleukin 1 (IL1β): IL1β is synthesized by mononuclear cells including synovial lining cells in the inflamed joint and by chondrocytes as an autocrine activity[1].

MMP: Early cartilage degeneration in OA is most likely the result of metalloproteinase enzymatic activity. Cartilage contains two families of metalloproteinase namely ADAMTs & MMPs.

Both families of metalloproteinases are upregulated in OA cartilage and both are highly expressed in OA.[1]

MMPs and ADAMTs play a major role in degradation of cartilage extracellular matrix. Several MMPs & ADAMTs are candidate targets for disease modification.

The Control of metalloproteinase activity in OA is complex with regulation occurring at three different levels; synthesis, secretion, activation of latent enzymes and inactivation by proteinase inhibitors.[1]

Most Metalloproteinase are not constitutively expressed but their transcription is induced after stimulation of cytokines and growth factor signaling. Once transcribed, the transcript stability and translation of several metalloproteinase (MMP13) are regulated by micro-RNA.[1]

Several of micro-RNA are controlled by the same cytokines and growth factor that maintain cartilage homeostasis including IL1β and TNF-α.

MMP13 may be the most important in OA because it preferentially degrade type II collagen. Hence, reduce the mechanical properties of the cartilage. Expression of MMP13 greatly increases in OA over all other collagenases.

Characteristic features of established osteoarthritis are the increased production of pro inflammatory cytokines such as IL1β, TNF-α by articular chondrocyte. Both IUD and TNF-α exert a cascade of stimulation of MMP13, and hence enhance cartilage degradation[1].

Nitric oxide (NO) produced by iNOS, is a major catabolic factor produced by chondrocyte in response to pro-inflammatory cytokines, such as Interleukin 1 beta (IL1β) and tumor necrosis factor alpha (TNF-α). Considerable evidence indicates that overproduction of NO by chondrocyte plays a major role in the perpetuation of cartilage destruction in knee OA[1]. Increased concentration of nitrite have been demonstrated in the synovial fluid of patients with KOA. Whereas normal cartilage does not express iNOS or produce NO without stimulation by cytokines such as IL1b[1].

Nitric oxide exerts multiple effects on chondrocyte that promote cartilage degeneration[1]. These include: inhibition of proteoglycan and collagen synthesis; activation of metalloproteinases[1]; increased susceptibility of other oxidants such as $H_2O_2$; and increased apoptosis.

iii. Garlic

Garlic (*Allium satium*) has been used by various cultures, as an antibiotic and an immune booster[2-4]. Garlic has strong antioxidant properties[5]. It has been suggested that garlic can prevent cardiovascular diseases, inhibit platelet aggregation, thrombus formation, prevent cancer,[5-7]. diseases associated with cerebral aging, arthritis, and cataract formation[5-8]. Garlic is composed of flavenols, selenium and sulphur compounds[2-4,7,9,10]. Some sulphur compounds decompose into a variety of thiosulfinates and polysulfides by the action of enzyme alinase. In addition to diallysulfide, diallyldisulfide and diallyltrisulfide[7,11,12]. These organo-sulphur compounds have very strong antioxidant properties[7,11,12]. Selenium has 3 major functions; reduction of organic and inorganic peroxide, metabolism of hydrogen peroxide which is intermediate step in the metabolism of prostaglandin and modulation of respiratory burst through the control of superoxide $O_2$ and hydrogen peroxide[13,14]. Eicosanoids synthesis is significantly diminished in the absence of selenium. It is likely that both anti-inflammatory and immune modulating effects of selenium are mediated by means of production of eicosanoids and reduction of hydroperoxides[14].

The high content of selenium and sulphur compounds in garlic would suggest its beneficiary effect in treating osteoarthritis. However, the use of garlic as an antioxidant in treatment of knee OA has not been extensively studied in the recent literature.

Selenium supplementation alone modulated inflammation and immune response at clinical and experimental level[15,16] Kurz et al.[10] found significant reduction of mice knee osteoarthritis with increased expression of glutathione peroxidase in synovium after intake of diet rich in selenium. Selenium improved indices of inflammation in experimental models such as adjuvant arthritis in rats or in the lupus mice[11]. Selenium intake resulted in reduction of pain, swollen and tender joints numbers in rheumatoid arthritis patients[12]. In the present study, we had similar results after garlic supplementation. In addition, to decline of cytokines in synovial fluids and improvement of muscular strength. This is because garlic is rich in selenium plus organosulphur compounds.

CLINICAL STUDIES

Study I: Effect of Combined Garlic Therapy and Comprehensive Rehabilitation Program versus Comprehensive Rehabilitation Program Alone on Control of Clinical Manifestations and Quality of Life of Knee Osteoarthritis Patients Study I Materials and Methods: Patients with knee OA were randomized to two groups, Group I received comprehensive rehabilitation program including diet modification, electrotherapy, resistance, and flexibility exercises for legs 3 times weekly for 8 weeks. Group II received the same rehabilitation program as Group I and in addition received daily Garlic capsules 900 mg for 8 weeks. Pain score was measured by visual analogue scale, Stanford health assessment questionnaire HAQ, One repetition maximum for muscles strength, body mass index and synovial fluid analysis of IL1b, IL6, TNF alpha and selenium, All these measured before and after the end of the study.

Study I Results: The results of this study have shown that body mass index significantly decreased among both groups without significant difference. Knee pain significantly decreased in group II receiving garlic therapy more than group I. One repetition maximum significantly increased in group II more than group I. Health assessment questionnaire improved in both groups but the percent change was more in Group II. Synovial fluid analysis revealed only significant drop of IL1b, IL6 and TNF alpha in Group II only. Also, selenium level significantly increased in Group II.

Study I Conclusion: This study supports the use of garlic as complementary treatment for knee osteoarthritis since it improves clinical and laboratory indices of inflammation, hence, the rehabilitation outcome.

Study II: Effect of Garlic versus Glucosamine Sulphate on Cartilage Degeneration and Clinical Manifestations of Knee Osteoarthritis Patients In the second study, I had compared the effect of garlic versus glucosamine on cartilage degeneration in knee osteoarthritis patients. I have chosen glucosamine sulfate to be the comparing drug due to its well known chondroprotective properties and it has been in the market for a while to control the symptoms of knee osteoarthritis.

Study II Materials and Methods: In this study there were two groups of patients suffering from knee osteoarthritis. both groups showed no significant difference regarding demographic data at the baseline. Garlic group receive 900 mg of garlic capsules daily for 8 weeks. The glucosamine group received 1500 mg glucosamine sulfate daily for 8 weeks. As regard baseline affection of knee in both groups. The garlic group has bilateral knee OA in 100% of patients and significant knee deformity compared to glucosamine group who were having only Bilateral knee affection in 70% of patients.

Study II Results: At the end of the study, the garlic group showed significant improvement of effusion compared to glucosamine sulfate. Pain score significantly improved in both groups with no difference between groups. Body mass index was comparable among both groups at the baseline and at the end of study, it did not significantly change but the glucosamine group has higher mean percent change than garlic group at the end of the study. There was no difference between both groups at base line regarding level of MMP13, collagenase and glutathione peroxidase. At the end of the study, both groups showed significant reduction of level of MMP13, collagenase and glutathione peroxidase with no difference between the groups.

Study II Conclusion: The effect of garlic in this study could be secondary to suppression of cytokines thus down regulate matrix metalloproteinases. In addition, garlic has very strong antioxidant action with ability to scavenge reactive oxygen species and ameliorate oxidative stress. This action of garlic is related to its content of organosulphur compounds. Garlic group had better control of knee effusion compared to glucosamine sulfate that could be due to stronger anti-inflammatory effect of garlic due to its effect on cytokines and free radicals. Additionally, there was significant reduction of MMP13 and collagenase, hence decrease cartilage degradation in both garlic and glucosamine group. Also, both groups had significant reduction in the level of glutathione peroxidase i.e., decrease the oxidative stress thus, less cartilage degeneration. Both garlic and glucosamine sulfate improve clinical manifestations and suppress cartilage degeneration in knee osteoarthritis patients.

Study III: Does the dose of garlic therapy affect its chondroprotective properties in knee osteoarthritis?

The aim of this study was to compare the effect of garlic in dose of 900 mg daily versus its effect in dose of 1800 mg daily on serum MMP13, IL1β, nitric oxide and selenium as well as clinical manifestations in knee osteoarthritis patients.

Study III Materials and Methods: In this study, patients with knee OA were randomly assigned into two groups; Group I received 1800 mg of garlic daily for 8 weeks and group II received 900 mg daily for 8 weeks which was the dose used in the previous two studies. Both groups were comparable regarding age and sex distribution with no statistical difference. As regards knee effusion and deformity, Group I had significantly higher effusion and deformity compared to Group II. Also group I had higher pain score at the beginning compared to group II. Body mass index also was significantly higher at baseline among Group I. At the end of the study, both groups showed significant reduction in pain score and functional status as measured by Lequesne Index, compared to their baseline. But Group I had higher significant reduction compared to Group II. Group I at the end of study group I showed significant reduction in body mass index.

Study III Results: At base line, level of serum IL1b was significantly higher in group I. While at the end of the study, both groups showed significant reduction of IL1B with group I showing more significant reduction compared to Group II. In regard TNF alpha, at baseline, Group I had significantly higher level of TNF alpha. At the end of the study, there was significant reduction of level of TNF alpha among both groups compared to base line, but still the level of reduction was significantly higher in Group I compared to Group II. In regard Nitric oxide level, at the base line the group I patients had significant higher level of NO. at the end of the study, both groups had significant reduction of NO but Group I had significantly higher level of reduction in NO compared to Group II. The level of MMP13 was comparable at the base line among both groups without difference. At the end of the study, MMP13 significantly dropped in both groups with group I having higher significant level of reduction compared to group II. Selenium level at the base line was significantly lower in group I. At the end of the study both group's had significant increase in level of selenium with higher significant increase among group I.

Study III Conclusion: In conclusion of this study, both doses of garlic therapy whether 900 mg or 1800 mg daily significantly controlled 1 the clinical manifestation of knee osteoarthritis, improve functional status of the patients. As well as control the progression of knee osteoarthritis through suppression of inflammatory cytokines; IL1b and TNF alpha and Nitric Oxide, cartilage degrading enzymes; namely MMP13. But the higher dose of garlic demonstrated significant higher effect among all these tested parameters. Hence, we can conclude that the higher dose of garlic namely 1800 mg daily has higher chondroprotective effect on patients with knee osteoarthritis.

From the above-mentioned studies; I concluded that: Garlic is very potent anti-inflammatory based on control of level of serum and synovial inflammatory cytokines mainly IL1B, IL6, Tumor necrosis factor Alpha and nitric oxide. That garlic is potent suppressor to cartilage degradation which is key process in the pathology of knee osteoarthritis. This effect of garlic is through suppression of collagenase and matrix metalloproteinases, the enzymes involving cartilage degradation in knee OA as well as suppression of cytokines that perpetuate the degrading enzymes, hence stop this viscous circle cascade of cartilage degeneration in knee osteoarthritis. Garlic has very strong antioxidant properties through suppression of glutathione peroxidase. Garlic has selenium which is known as mentioned above to control inflammation. The studies proven the increase in the level of selenium at the end, which could partly why garlic improve inflammation, in addition to the presence of organo-Sulphur compounds within the garlic, which makes the garlic supplement is higher than using selenium tablet it alone. Garlic control knee pain and relieves the inflammation evidenced by resolution of effusion. Garlic improve muscles strength in patient with knee OA this was evidence by improvement of one repetition maximum, the measure of the muscle strength and this could be explained by as garlic improve and control the knee pain and inflammation, the patients were able to do more strengthening exercise, hence at the end of the study the group receiving garlic got more muscle strength. Garlic has led to improvement of the quality of life of those patients receiving garlic therapy. This is the ultimate goal after controlling the knee pain and inflammation and better muscle strength so patient can participate in daily living activities with ease. Hence, better quality of life. Garlic proved a comparable effect as glucosamine sulphate without any harmful side effect being a natural nutrient substance. The dose of garlic therapy use of 1800 mg daily was proven to be more significantly effective in controlling all the above-mentioned effect of garlic on knee osteoarthritis although the dose of 900 mg daily still showed significant effect but this this more effective and as long as no harm of the use of this high dose since garlic is natural therapy, so I do recommend the use of this higher dose for more cartilage protection.

CITED REFERENCES

1—Paul E Di Cesare, Dominik R Haudenschild, Jonathan Samuels, Steven A Abramson. *Pathogenesis of osteoarthritis*. Chapter 98 In Kelly & Firestein 'S Textbook of Rheumatology. Tenth Edition, Publisher Elsevier, 2017. Page 1685-1704

2—Czajka D M & Narin S (1984)*Minerals*. In: Krause, Mahan (eds.) Food, Nutrition and diet therapy (7thedn.) Saunders WB Company.

3—Chang C, Gershwin E (2000) *The anti-inflammatory effects of Chinese herbs, plants, spices*. In: Genhwin M E, German J B, Keen C L (eds.) Nutrition and immunology principles and practice. Human, Press Totowa, New Gersy.

4-. Elhusseiny A (2004) *The curing garlic, Disease killer and energizer*. Dar El-Talae for publishing, distributing and exporting Cairo. 2004.

5-. Rahman K (2003) Garlic and aging: new insights into an old remedy. Ageing Res Rev 2: 39-56.

6-. Rahman K, Lowe G M (2006) *Garlic and cardiovascular disease: a critical review*. J Nutr 136: 736S-740S.

7-. Lanzotti V (2006) *The analysis of onion and garlic*. J Chromatogr A 1112: 3-22.

8-. Ali M, Thomson M, Afzal M (2000) *Garlic and onions: their effect on eicosanoid metabolism and its clinical relevance*. Prostaglandins Leukot Essent Fatty Acids 62: 55-73.

9. Arnault I, Auger J (2006) *Seleno-compounds in garlic and onion*. J Chromatogr A 1112: 23-30.
10. Dumont E, Vanhaecke F, Cornelis R (2006) *Selenium speciation from food source to metabolite: a critical review*. Annal Bioanal Chem 385:1304-23.
11-. Augusti K T (1996) Therapeutic values of onion (*Allium cepa* L.) and garlic (*Allium sativum* L.). Indian J Exp Biol 34: 634-640.
12—Atmaca G (2004) Antioxidant effects of sulfur-containing amino acids. Yonsei Med J 45: 776-788.
13—Altman R, Asch E, Bloch D, Bole G, Borenstein D, et al. (1986) Development of criteria for the classification and reporting of osteoarthritis. Classification of osteoarthritis of the knee. Diagnostic and Therapeutic Criteria Committee of the American Rheumatism Association. Arthritis Rheum 29: 1039-1049.
14—Lee A J (2001) *Glucosamine, chondroitin sulphate, and other alternative pharmacologic approaches to treating osteoarthritis*. In: Todd P, Stitik (eds.) Physical Medicine and Rehabilitation; osteoarthritis, State of the art reviews. Hanley & Belfus, inc., Philadelphia.
15—Ryan-Harshman M, Aldoori W (2005) The relevance of selenium to immunity, cancer, and infectious/inflammatory diseases. Can J Diet Pract Res 66: 98-102.
16—Kurz B, Jost B, Schünke M (2002) Dietary vitamins and selenium diminish the development of mechanically induced osteoarthritis and increase the expression of antioxidative enzymes in the knee joint of STR/1N mice. Osteoarthritis Cartilage 10: 119-126.
17—Parnham M, Winkelmann J, Leyck S (1983) Macrophage, lymphocyte and chronic inflammatory response in selenium deficient rodents. Association with decreased glutathione peroxidase activity. Int J Immunopharmacol 5: 455-461.
18—Peretz A, Neve J, Duchateau J, Famaey J P (1992) Adjuvant treatment of recent onset rheumatoid arthritis by selenium supplementation: preliminary observations. Br J Rheumatol 31: 281-282.
19—Topp R, Woolley S, Hornyak J 3rd, Khuder S, Kahaleh B (2002) The effect of dynamic versus isometric resistance training on pain and functioning among adults with osteoarthritis of the knee. Arch Phys Med Rehabil 83: 1187-1195.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for treating a knee osteoarthritis patient using an oral dried garlic supplement, wherein the method for treating comprises:
   a. performing an initial synovial fluid analysis and an initial serum analysis on the knee osteoarthritis patient thereby defining a set of initial results;
   b. performing a second initial synovial fluid analysis and a second initial serum analysis on a second knee osteoarthritis patient thereby defining a second set of initial results;
   c. wherein the initial synovial fluid analysis and second initial synovial fluid analysis each comprise measuring a level of a plurality of inflammatory cytokines and a plurality of inflammatory markers comprising IL1β, IL6, TNF-α, and nitric oxide ("NO");
   d. administering to the knee osteoarthritis patient 1800 mg of the oral dried garlic supplement on a daily basis and for eight weeks or more;
   administering to the second knee osteoarthritis patient 900 mg of the oral dried garlic supplement on a daily basis and for a second eight weeks or more;
   f. after the eight weeks or more, performing a final synovial fluid analysis and a final serum analysis on the knee osteoarthritis patient thereby defining a set of final results;
   g. after the second eight weeks or more, performing a second final synovial fluid analysis and a second final serum analysis on the second knee osteoarthritis patient thereby defining a second set of final results;
   h. wherein, after administering the 1800 mg of the oral dried garlic supplement to the knee osteoarthritis patient, the level of the plurality of inflammatory markers and the plurality of inflammatory cytokines from the set of final results is reduced by greater than 80% when compared to the set of initial results;
   i. wherein, after administering the 900 mg of the oral dried garlic supplement to the second knee osteoarthritis patient, the level of the plurality of inflammatory markers and the plurality of inflammatory cytokines from the second set of final results is reduced by greater than 50% when compared to the second set of initial results;
   j. wherein the level of the plurality of inflammatory markers and the plurality of inflammatory cytokines in the set of final results after administering the 1800 mg of the oral dried garlic supplement to the knee osteoarthritis patient is statistically significantly lower when compared to the level of inflammatory markers and inflammatory cytokines of the second set of final results measured after administering 900 mg of the oral dried garlic supplement to the second knee osteoarthritis patient.

2. The method of claim 1, wherein the initial serum analysis, the second serum analysis, and the final serum analysis, and the second final serum each comprise measuring a level of cartilage degrading enzymes comprising MMP13, wherein:
   (i) after administering 900 mg of the oral dried garlic supplement to the second knee osteoarthritis patient, the level of cartilage degrading enzymes is reduced by above 50% when compared to the level of cartilage degrading enzymes of the second initial serum analysis;
   (ii) after administering the 1800 mg of the oral dried garlic supplement to the knee osteoarthritis patient, wherein the level of cartilage degrading enzymes of the final serum analysis is reduced by greater than 80% when compared to the level of cartilage degrading enzymes of the initial serum analysis; and
   (iii) after administering the 1800 mg of the oral dried garlic supplement to the knee osteoarthritis patient, the level of cartilage degrading enzymes of the final serum analysis of the knee osteoarthritis patient is statistically significantly lower than the level of cartilage degrading enzymes of the second final serum analysis of the second knee osteoarthritis patient.

3. The method of claim 2, wherein the method comprises:
   (i) measuring an initial Lequesne index functional score when performing the initial synovial fluid analysis on the knee osteoarthritis patient, and wherein after the eight weeks or more, measuring a final Lequesne index functional score when performing the final synovial fluid analysis on the knee osteoarthritis patient;

(ii) measuring a second initial Lequesne index functional score when performing the second initial synovial fluid analysis on the second knee osteoarthritis patient, and wherein after the second eight weeks or more, measuring a second final Lequesne index functional score when performing the second final synovial fluid analysis on the second knee osteoarthritis patient;

(iii) measuring a final Lequesne index functional score for the knee osteoarthritis patient after the eight weeks or more of administering the 1800 mg of the oral dried garlic supplement to the knee osteoarthritis patient;

(iv) measuring a second final Lequesne index functional score for the second knee osteoarthritis patient after the second eight weeks or more of administering the 900 mg of the oral dried garlic supplement to the second knee osteoarthritis patient;

(v) wherein the final Lequesne index functional score of the knee osteoarthritis patient is improved by greater than 80% when compared to the initial Lequesne index functional score of the knee osteoarthritis patient;

(vi) wherein the second final Lequesne index functional score of the second knee osteoarthritis patient is improved by greater than 50% when compared to the second initial Lequesne index functional score of the second knee osteoarthritis patient;

(vii) wherein the final Lequesne index functional score of the knee osteoarthritis patient is statistically significantly improved when compared to the second final Lequesne index functional score of the second knee osteoarthritis patient;

(iii) the final Lequesne index functional score in administering the 1800 mg of the oral dried garlic supplement is statistically significantly improved relative to the final Lequesne index functional score in administering the 900 mg of the oral dried garlic supplement.

4. The method of claim 3, wherein the initial synovial fluid analysis, the second initial synovial fluid analysis, the final synovial fluid analysis and the second final synovial fluid analysis each comprise measuring a level of glutathione peroxidase, wherein:

(i) after administering the 1800 mg of the oral directed garlic supplement to the knee osteoarthritis patient, wherein the level of glutathione peroxidase of the final synovial fluid analysis is improved by greater than 80% when compared to the level of glutathione peroxidase of the initial synovial fluid analysis of the knee osteoarthritis patient;

(ii) after administering the 900 mg of the oral directed garlic supplement to the second knee osteoarthritis patient, wherein the level of glutathione peroxidase of the second final synovial fluid analysis is improved by greater than 50% when compared to the level of glutathione peroxidase of the second initial synovial fluid analysis of the second knee osteoarthritis patient; and (iii) after administering the 1800 mg of the oral dried garlic supplement to the knee osteoarthritis patient, the level of glutathione peroxidase of the final synovial fluid analysis is statistically significantly improved when compared to the level of glutathione peroxidase of the second final synovial fluid analysis of the second osteoarthritis patient when compared to the second initial synovial fluid analysis of the second osteoarthritis patient.

5. The method of claim 4, wherein the initial synovial fluid analysis, the second initial synovial fluid analysis, the final synovial fluid analysis and the second final synovial fluid analysis each comprise measuring a concentration of selenium, wherein:

(i) after administering the 1800 mg of the oral dried garlic supplement to the knee osteoarthritis patient, the level of selenium of the final synovial fluid analysis is increased by greater than 80% when compared to the level of selenium of the initial synovial fluid analysis of the knee osteoarthritis patient;

(ii) after administering the 900 mg of the oral dried garlic supplement to the second knee osteoarthritis patient, the level of selenium of the second final synovial fluid analysis is increased by greater than 50% relative to the level of selenium of the second initial synovial fluid analysis of the second knee osteoarthritis patient;

(iii) after administering the 1800 mg of the oral dried garlic to the knee osteoarthritis patient, the level of selenium of the final synovial fluid analysis for the knee osteoarthritis patient is statistically significantly increased when compared to the level of selenium of the second final synovial fluid analysis of the second osteoarthritis patient-relative to the second initial synovial fluid analysis of the second osteoarthritis patient.

* * * * *